United States Patent [19]
Kahn

[11] Patent Number: 5,674,976
[45] Date of Patent: Oct. 7, 1997

[54] CONFORMATIONALLY RESTRICTED MIMETICS OF GAMMA TURNS AND PEPTIDES CONTAINING THE SAME

[76] Inventor: Michael Kahn, 950 W. Berwyn St., Unit 12, Chicago, Ill. 60640

[21] Appl. No.: 486,281

[22] Filed: Jun. 6, 1995

Related U.S. Application Data

[62] Division of Ser. No. 208,801, Mar. 9, 1994, Pat. No. 5,440,013, which is a continuation of Ser. No. 983,607, Nov. 30, 1992, abandoned, which is a continuation of Ser. No. 651,800, Feb. 7, 1991, abandoned.

[51] Int. Cl.$^6$ .............................. A61K 38/12; C07K 5/00
[52] U.S. Cl. ...................... 530/317; 514/11; 530/323; 530/333
[58] Field of Search .......................... 530/317, 323, 530/333; 514/11

[56] References Cited

U.S. PATENT DOCUMENTS

| | | |
|---|---|---|
| 4,699,898 | 10/1987 | Gottlieb . |
| 4,908,203 | 3/1990 | Thornton . |
| 5,475,085 | 12/1995 | Kahn ...................................... 530/317 |

FOREIGN PATENT DOCUMENTS

| | | |
|---|---|---|
| WO 91/05564 | 5/1991 | WIPO . |
| WO 92/20704 | 11/1992 | WIPO . |

OTHER PUBLICATIONS

Kahn and Chen, "Methodology for the Synthesis of Mimetics of Peptides β-turns," *Tetrahedron Letters* 28(15): 1623–1626, 1987.

Kahn et al., "Nonpeptide Mimetics of β–Turns: A Facile Oxidative Intramolecular Cycloaddition of an Azodicarbonyl System," *Journal of the American Chemical Society* 110: 1638–1639, 1988.

Kahn et al., "The Design and Synthesis of Mimetics of Peptide β–turns," *Journal of Molecular Recognition* 1(2): 75–79, 1988.

Kahn and Bertenshaw, "The Incorporation of β3–Turn Prosthetic Units Into Merrifield Solid Phase Peptide Synthesis," *Tetrahedron Letters* 30(18): 2317–2320, 1989.

Kahn et al., "The Design and Synthesis of a Nonpeptide Mimic of Erabutoxin," *Heterocycles* 25:29–31, 1987.

Kahn and Devens, "The Design and Synthesis of a Nonpeptide Mimic of an Immunosuppressing Peptide," *Tetrahedron Letters* 27(40): 4841–4844, 1986.

Ball and Alewood, "Conformational Constraints: Nonpeptide β–Turn Mimics," *Journal of Molecular Recognition* 3(2): 55–64, 1990.

Freidinger et al., "Bioactive Conformation of Luteinizing Hormone–Releasing Hormone: Evidence from a Conformationally Constrained Analog," *Science* 210: 656–658, 1980.

Kemp and Stites, "A convenient preparation of derivatives of 3(S)–amino–10(R)–carboxy–1,6–diaza–cyclodeca–2, 7–dione. The dilactam of L–α, γ–diaminobutyric acid and D–glutamic acid: a β–turn template," *Tetrahedron Letters* 29(40): 5057–5060, 1988.

Miller et al., "Synthesis of β3–Lactams from Substituted Hydroxamic Acids," *Journal of American Chemical Society* 102: 7026–7032, 1980.

Olson et al., "Design and Synthesis of a Protein β–Turn Mimetic," *J. Am. Chem. Soc.* 112: 323–333, 1990.

Arrhenius and Satterthwait, "The substitution of an amide–amide backbone hydrogen bond in an α–helical peptide with a covalent hydrogen bond mimic," in *Proceedings of the American Peptide Symposium*, 1990, pp. 870–872.

Carpino et al., "((9–Fluorenylmethyl)oxy)carbonyl (FMOC) Amino Acid Fluorides. Convenient New Peptide Coupling Reagents Applicable to the FMOC/tert–Butyl Strategy for Solution and Solid–Phase Syntheses," *J. Am. Chem. Soc.* 112: 9651–9652, 1990.

Chang et al., "A Potent Nonpeptide Cholecystokinin Antagonist Selective for Peripheral Tissues Isolated from *Aspergillus alliaceus*," *Science* 230:177–179, 1985.

Chen et al., "Design and synthesis of a CD4 βturn mimetic that inhibits human immunodeficiency virus envelope glycoprotein gp 120 binding and infection of human lymphocytes," *Proc. Natl. Acad Sci. USA* 89: 5872–5876, 1992.

Chipkin et al., "Analgesics," *Ann. Rep. Med. Chem.* 23:11–18, 1988.

Corey and Fuchs, "A Synthetic Method for Formyl→Ethynyl Conversion (RCHO→RC≡CH or RC≡CR')," *Tetrahedron Lett.* 36: 3769–3772, 1972.

Fauchere, J., "Elements for the Rational Design of Peptide Drugs," *Adv. in Drug. Res.* 15: 29–69, 1986.

Ferreira et al., "Isolation of Bradykinin–Potentiating Peptides from *Bothropsjararaca* Venom," *Biochemistry* 9: 2583, 1970.

Gilon et al., "Backbone Cyclization: A New Method for Conferring Conformational Constraint on Peptides," *Biopolymers* 31: 745–750, 1991.

Goel et al., "N–tert–Butoxycarbonyl–L–Leucinal (Carbamic acid, (1 –formyl–3–methylbutyl)–,1,1–dimethylethyl ester, (S)–)," *Org. Syn.* 67: 69–75, 1988.

Gribble and Nutaitis, "Sodium Borohydride in Carboxylic Acid Media. A Review of the Synthetic Utility of Acyloxyborohydrides," *Org. Prep. Proced. Int.* 17:317–384, 1985.

Hart and Ha, "The Ester Enolate–Imine Condensation Route to β–Lactams," *Chem. Rev.* 89 1447–1465, 1989.

Hoffman et al., "The Preparation of 2–Hydrazinyl Esters in High Optical Purity from 2–Sulfonyloxy Esters," *Tetrahedron Letters* 31(21): 2953–2956, 1990.

(List continued on next page.)

*Primary Examiner*—Paula K. Hutzell
*Assistant Examiner*—Benet Prickril

[57] ABSTRACT

The invention provides materials and methods for synthesizing novel beta-turn mimetics, as well as the novel beta-turn mimetics themselves, and peptides containing the same. Also provided are novel synthetic nonpeptide therapeutic molecules designed upon the interactions between beta-turn mimetics or peptides containing the same, and receptors or enzymes.

8 Claims, 2 Drawing Sheets

OTHER PUBLICATIONS

House and Rasmusson, "Stereoselective Synthesis of α-Substituted α,β-Unsaturated Esters," *J. Org. Chem.* 26: 4278–4281, 1961.

Hruby et al., "Emerging approaches in the molecular design of receptor–selective peptide ligands: conformational, topographical and dynamic considerations," *Biochem. J.* 268:249–262, 1990.

Hruby, V., "Implications of the X–ray structure of deamino–oxytocin to agonist/antagonist–receptor interactions," *Trends Pharmacol. Sci.* 8: 336–339, 1987.

Krstenansky et al., "A New Approach to Conformationally Restricted Peptide Analogs: Rigid β–Bends. 1. Enkephalin as an Example," *Biochem. Biophys. Res. Commun.* 109(4): 1368–1374, 1982.

Lindlar, H., "Ein Neuer Katalysator für selektive Hydrierungen," *Helv. Chim. Acta* 35(57): 446–450, 1952.

Marshall et al., "Peptide Conformation and Biological Activity," *Ann. Rep. Med Chem.* 13 227–238, 1978.

Morgan et al., "Approaches to the Discovery of Non–Peptide Ligands for Peptide Receptors and Peptidases," *Ann. Rep. Med. Chem.* 24: 243–252, 1989.

Rajeswari et al., "A New Synthesis of Amides from Acyl Fluorides and N–Silylamines," *Tetrahedron Letters* 28(43): 5099–5102, 1987.

Römer et al., "An opioid benzodiazepine," *Nature* 298: 759–760, 1982.

Salzmann et al., "A Stereocontrolled Synthesis of (+)–Thienamycin," *J. Am. Chem. Soc.* 102: 6161–6163, 1980.

Sargovi et al., "Design and Synthesis of a Mimetic from an Antibody Complementarity–Determining Region," *Science* 253: 792–793, 1991.

Sasaki and Coy, "Solid Phase Synthesis of Peptides Containing the $CH_2NH$ Peptide Bond Isostere," *Peptides* 8:119–121, 1987.

Satterthwait et al., "Polypeptides stabilized by covalent hydrogen bond replacements," *Chem. Abst.* 112: 179892y, 1990.

Spatola, A., "Peptide Backbone Modifications: A Structure–Activity Analysis of Peptides Containing Amide Bond Surrogates. Conformational Constraints, and Rela . . . ," in *Chemistry and Biochemistry of Amino Acids, Peptides, and Proteins 7*, Weinstein, Ed., Marcel Dekker, New York, 1983, pp. 276–357.

Valle et al., "Crystal–state structural analysis of two γ–lactam–restricted analogs or Pro–Leu–Gly–$NH_2$," *Int. J. Peptide Protein Res.* 33: 181–190, 1989.

Wasserman et al., "Transamidation Reactions Using β–Lactams. The Synthesis of Homaline," *Tetrahedron Lett.* 23: 465–68, 1982.

Williams et al., "Syntheses and X–ray Crystal Structure Determination of 1,3–Bridged Beta–Lactams," *Journal of the American Chemical Society* 111: 1073–1081, 1989.

CONFORMATIONALLY RESTRICTED MIMETICS OF GAMMA TURNS AND PEPTIDES CONTAINING THE SAME

This application is a division of U.S. application Ser. No. 8/208,801 filed Mar. 9, 1994, now U.S. Pat. No. 5,440,013; which is a continuation of U.S. application Ser. No. 07/983,607 filed Nov. 30, 1992, now abandoned, which is a continuation of U.S. application Ser. No. 07/651,800 filed Feb. 7, 1991, now abandoned.

This was supported in part by National Science Foundation Grant CHE-8657046 and National Institute of Health Grant GM38260. The United States government may have certain rights in this invention.

BACKGROUND OF THE INVENTION

1. Field of the Invention

The invention relates to peptide mimetics, which are chemical structures which serve as appropriate substitutes for peptides in interactions with receptors and enzymes. The invention also relates to means for analyzing specific interactions between peptides and enzymes or receptors, as well as for developing new therapeutic agents, through the use of peptide mimetics.

2. Summary of the Related Art

Peptides and proteins play critical roles in the regulation of all biological processes. Peptides, for example, play a regulatory role as hormones and inhibitors, and are also involved in immunological recognition. The significant biological role of peptides makes important the understanding of the interactions between peptides and their receptors or enzymes to which they bind.

The determination of the receptor-bound conformation of a peptide is invaluable for the rational design of peptide analogues. However, Marshall et al., Ann. Rep. Med. Chem. 13:227-238 (1978), discloses that peptides are characteristically highly flexible molecules, the structures of which are strongly influenced by the environment in which they reside. Thus peptides are not generally useful for determining their receptor-bound conformation.

As no approach is available to predict a priori which new ligand-receptor interactions will lead to antagonists and which will lead to agonists of greater or less potency, it is necessary to perform classical structure-function studies in a systematic way to provide information about the specific amino acid residues and functional groups in a peptide that are important to biological activity. Studies of this nature can utilize conformationally constrained peptide mimetics. For example, Hruby, Trends Pharmacol. Sci. 8: 336-339 (1987), suggests that conformational constraints can provide information about the different requirements that a receptor has for a ligand to be an agonist or antagonist.

Generally, peptide mimetics can be defined as structures which serve as appropriate substitutes for peptides in interactions with receptors and enzymes. The development of rational approaches for discovering peptide mimetics is a major goal of medicinal chemistry. Such development has been attempted both by empirical screening approaches and by specific synthetic design.

Screening of pure chemical entities has been of quite limited utility for discovering peptide mimetics. However, Chipkin et al., Ann. Rep. Med. Chem. 23: 11 (1988), discloses discovery of ligands for the mu-opioid receptor by this approach; as does Romar et al., Nature 298: 760 (1982), for the kappa-opioid receptor.

Screening of complex mixtures of natural products has generally been more successful, especially for the discovery of peptidase inhibitors. For example, Ferreira et al., Biochemistry 9: 2583 (1970), discloses the discovery of the ACE inhibitor, teprotide, by screening the venom of Bothrops iaraca. This approach may also be applied to the discovery of receptor ligands. Chang et al., Science 230: 177 (1985), discloses the discovery of the CCK antagonist asperlicin, using this approach.

Specific design of peptide mimetics has utilized both peptide backbone modifications and chemical mimics of peptide secondary structure. Spatola, *Chemistry and Biochemistry of Amino Acids, Peptides and Proteins*, Vol. VII (Weinstein, Ed.) Marcel Dekker, New York (1983), p. 267, exhaustively reviews isosteric amide bond mimics which have been introduced into biologically active peptides. The beta-turn has been implicated as an important site for molecular recognition in many biologically active peptides. Consequently, peptides containing conformationally constrained mimetics of beta-turns are particularly desirable. Such peptides have been produced using either external or internal beta-turn mimetics.

External beta-turn mimetics were the first to be produced. Friedinger et al., Science 210: 656-658 (1980), discloses a conformationally constrained nonpeptide beta-turn mimetic monocyclic lactam that can readily be substituted into peptide sequences via its amino and carboxy termini, and that when substituted for $Gly^6$-$Leu^7$ in luteinizing hormone releasing hormone (LHRH), produces a potent agonist of LHRH activity.

Monocyclic lactams have generally been useful as external beta-turn mimetics for studying receptor-peptide interactions. However, the mimetic skeleton in these molecules is external to the beta-turn, which gives rise to numerous limitations. Chief among these is bulkiness, which requires the use of dipeptide mimetics, rather than mimetics of all four residues in an actual beta-turn. Substantial flexibility retained in these beta-turn mimetics makes it unsafe to assume that expected conformations are present, absent considerable conformational analysis. For example, Vallee et al., Int. J. Pept. Prot. Res. 33: 181-190 (1989), discloses that a monocyclic lactam beta-turn mimetic did not contain an expected type II' beta-turn in its crystal structure. Another limitation of the monocyclic Lactam beta-turn mimetics arises from the difficulty of producing molecules that effectively mimic the side chains of the natural peptide. These difficulties arise from steric hindrance by the mimetic skeleton, which results in a more effective mimic of the peptide backbone than of the side chains. Considering the great importance of side chains in receptor binding, these difficulties strongly limit the versatility of monocyclic lactams.

Although the use of bicyclic lactams reduces problems of flexibility somewhat, conformational analysis of peptides containing these mimetics may still be desirable. Moreover, the side chain hindrance in these molecules may be even worse than that in the monocyclic lactams. Finally, both monocyclic and bicyclic lactams mimic only type II and type II' beta-turns, whereas type I and type III beta-turns are more prevalent in proteins and presumably in peptides.

The limitations presented by external beta-turn mimetics may be minimized by using mimetics in which the mimetic skeleton approximately replaces the space that was occupied by the peptide backbone in the natural beta-turn. Such molecules are known as internal beta-turn mimetics. Internal beta-turn mimetics may not generally reproduce the geometry of the peptide backbone of the particular beta-turn as accurately as external beta-turn mimetics. However, the internal position of the constraint allows replacement of larger sections of peptide, thus making tetrapeptide mimetics possible. The lack of bulk also diminishes the likelihood of steric hindrance of the side chains by the mimetic skeleton.

Internal beta-turn mimetics having biological activity are known in the art. For example, Krstenasky et al., Biochem. Biophys. Commun. 109: 1368–1374 (1982), discloses a leucine enkephalin analog in which an internal beta-turn mimetic replaced the residues $Gly^2$-$Gly^3$-$Phe^4$-$Leu^5$, and which acted as an analgesic with one-third the potency of morphine. Other internal beta-turn mimetics have been described.

Kahn et al., Tetrahedron Lett. 27: 4841–4844 (1986), discloses an internal beta-turn mimetic, based upon an indolizidinone skeleton, and designed to mimic the lysine and arginine side-chain disposition of the immunosuppressing tripeptide Lys-Pro-Arg.

Kahn et al., Heterocycles 25: 29–31 (1987), discloses an internal beta-turn mimetic, based upon an indolizidinone skeleton, and designed to correctly position the aspartyl and arginyl side chains of a beta-turn in the proposed bioactive region of erabutoxin.

Kahn et al., Tetrahedron Lett. 28: 1623–1626 (1987), discloses a type I beta-turn mimetic which can be incorporated into a peptide via its amino and carboxy termini, and which is designed to mimic an idealized type I beta-turn. See also Kahn et al., J. Am. Chem. Soc. 110: 1638–1639 (1988): Kahn et al., J. Mol. Recogn. 1: 75–79 (1988).

Similarly, Kemp et al., Tetrahedron Lett. 29: 5057–5060 (1988), discloses a type II beta-turn mimetic which can be incorporated into a peptide via its amino and carboxy termini.

Arrhemius et al., Proc. Am. Peptide Syrup., Rivier and Marshall, Eds., Escom, Leiden (1990), discloses substitution or an amide-amide backbone hydrogen bond with a covalent hydrogen bond mimic to produce an alpha-helix mimetic.

Thus, there have been numerous successes in obtaining mimetics which can force or stabilize peptide secondary structure. However, little success has been reported in incorporating mimetics at the active site of a peptide hormone or neurotransmitter, probably because of the difficulty of producing mimetics that possess appropriately positioned side chain groups. There is therefore, a need for improved mimetics having greater substituent flexibility to allow for easy synthesis of mimetics having appropriately positioned side chain groups. Moreover, there is a need for improved mimetics having more readily controllable skeletal sizes and angles, so that different types of beta-turn structures can be easily imitated. An ideal mimetic would provide ready control and variation of both side chain positioning and mimetic skeleton size and angles through a modular construction system that allows easy synthesis of a wide variety of mimetics.

For recent reviews of the related art, see Hruby et al., Biochem. J. 268: 249–262 (1990); Ball et al., J. Mol. Recogn. 3: 55–64 (1990); Morgan et al., Ann. Rep. Med. Chem. 24: 243–252 (1989); and Fauchere, Adv. Drug Res. 15: 29–69 (1986).

BRIEF SUMMARY OF THE INVENTION

The invention provides materials and methods for the synthesis of beta-turn mimetics. More particularly, the invention provides a modular system for synthesizing beta-turn mimetics having nearly infinite variability in degree of conformational constraint, flexibility, side chain constituents, and in the size and bond angles of the mimetic skeleton. The materials and methods of the invention are readily amenable to incorporation in conventional peptide synthesis procedures.

In a first aspect, the invention provides modular component pieces for the assembly of beta-turn mimetics. In a second aspect, the invention provides methods for making the beta-turn mimetics and for making peptides containing the same. In a third aspect, the invention provides novel beta-turn mimetics and novel peptide structures containing such beta-turn mimetics. In a fourth aspect the invention provides novel synthetic-nonpeptide therapeutic molecules.

The materials and methods of the invention are useful for probing the molecular interactions between ligands and receptors, and thus for providing therapeutic agonists and antagonists capable of interacting with receptors or enzymes.

Additional preferred embodiments of the invention will be made apparent by the following detailed description, examples, and claims.

DETAILED DESCRIPTION OF THE SPECIFIC EMBODIMENTS

The invention provides a modular system for producing beta-turn mimetics having a virtually limitless range of skeletal sizes and bond angles, and side chain substituents. Beta-turn mimetics according to the invention can thus have changed side chain substituents without having any changes in the backbone conformation. Moreover, beta-turn mimetics according to the invention possess appropriate termini for incorporation into peptides by standard peptide synthesis procedures. Thus the invention provides a system for producing a virtually unlimited array of peptides having beta-turn mimetics according to the invention incorporated therein. For purposes of the invention the term "beta turn mimetics" is sometimes used in a general sense, and is intended to encompass mimetics of beta turns, gamma turns, beta hairpins, and beta bulges, all of which are provided by the invention by varying the modular component pieces used.

In a first aspect, the invention provides modular component pieces for the construction of beta-turn mimetics. Modular component pieces according to the invention include both L- and D-enantiomeric forms. A first modular component piece according to the invention is characterized by the structural formula

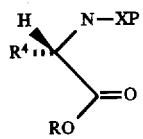

wherein $R^4$ may be any naturally-occurring amino acid side chain substituent, or analog thereof, wherein P is a protective group suitable for use in peptide synthesis, and wherein the linker moiety, X comprises a linker terminating in an amino or hydrazino group, and wherein the termini of the linker are separated by zero to ten carbon atoms, and where the carbon atoms involved in carbon-carbon or carbon-nitrogen bonds may be saturated, unsaturated, or aromatic. Specific preferred examples of such linkers are shown in FIG. 2.

The linker group X may be varied in size and or flexibility to control the conformation of the ring in the final mimetic. This allows the construction in a predictable fashion of a nearly infinite variety of conformationally restricted ligands. Ligands having maximum biological activity can then be subjected to spectroscopic and computer-assisted molecular modeling to determine the bound confirmation.

Figure 1:
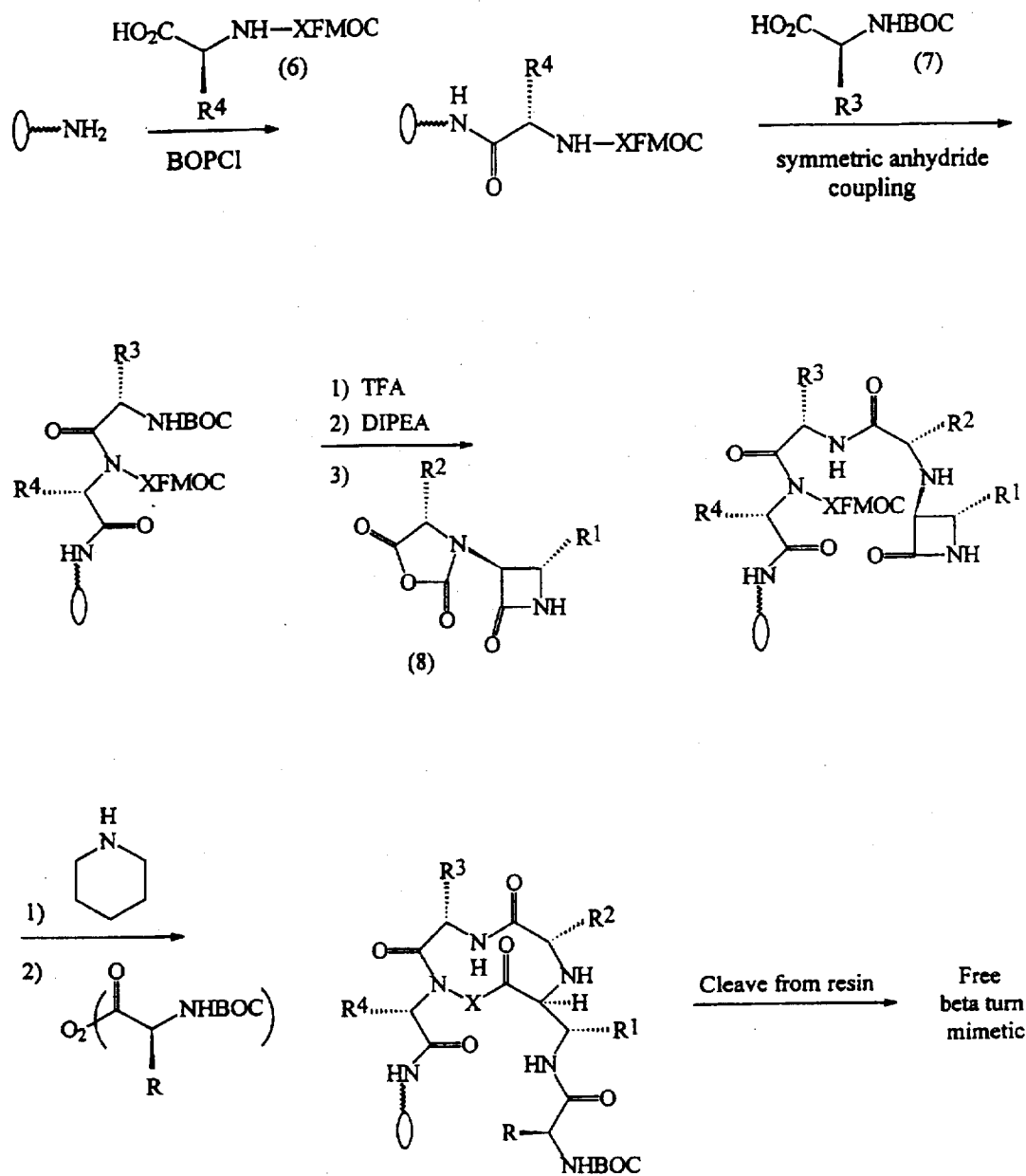
FIG. 1 shows a route for synthesizing either a beta-turn mimetic according to the invention, or a novel peptide containing the same, utilizing the modular component pieces of the invention in a standard Merrifield synthesis scheme.

Such first component piece may be synthesized according to alternative routes, depending on the nature of the X groups. According to a first route, as shown in FIG. 1, the component is synthesized by the SN2 displacement of an alpha-triflyoxy ester which is readily produced from the corresponding amine acid according to procedure described by Hoffman and Kim, Tetrahedron Lett. ;31: 2953 (1990).

Figure 2:
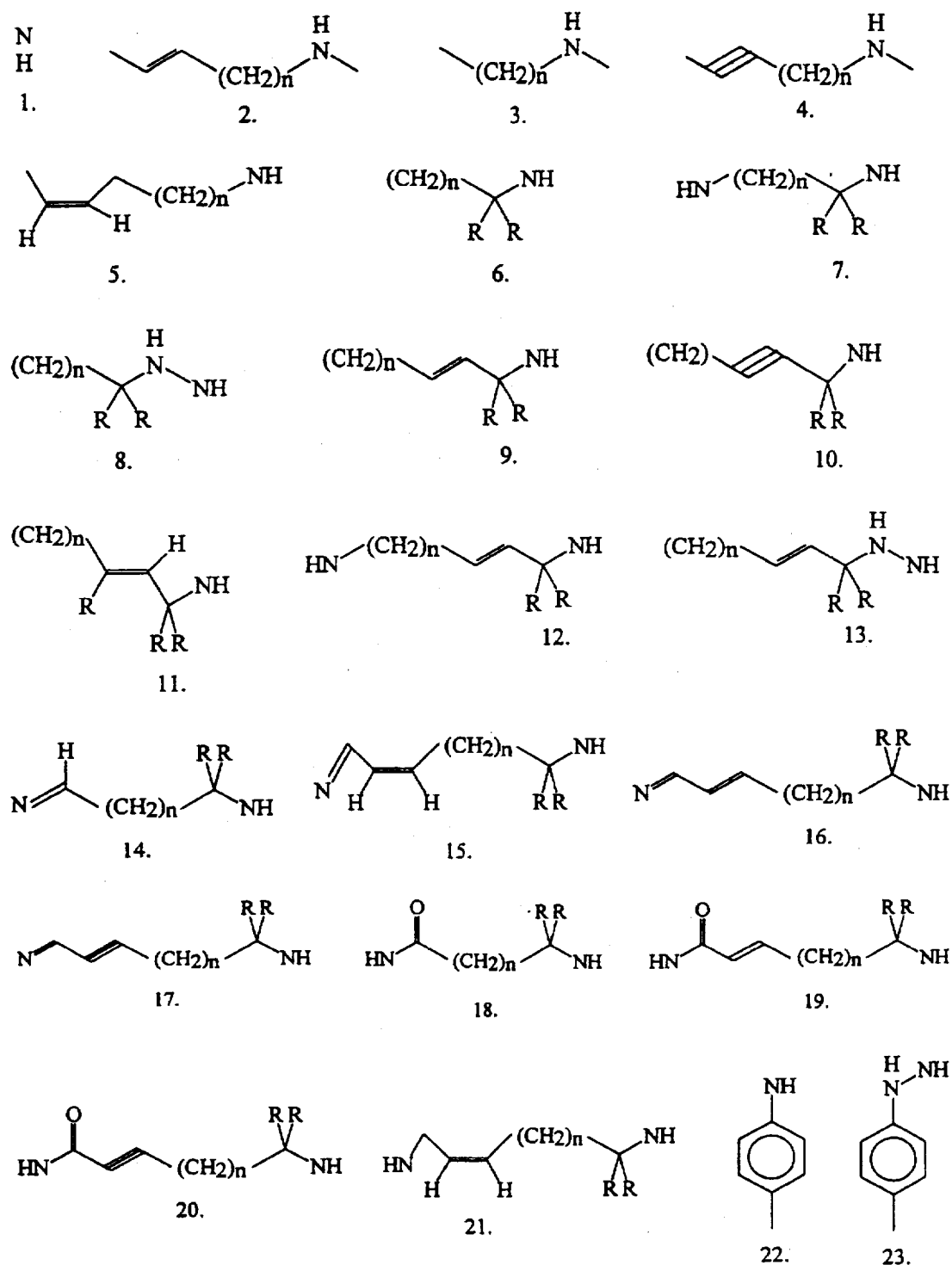
FIG. 2 shows preferred embodiments of the linker moiety, X, of the first modular component piece. For each linker shown, n=0–4 and R=H or $CH_3$. Aromatic linkers are shown in para configuration, but may alternatively be in ortho or meta configuration.

An alternative route for synthesis of the first component piece is shown in FIG. 2 and utilizes a quite facile reductive amination reaction, as described by Gribble and Nutaitis, Org. Prep. Proced. Int. 17: 317, A85 and Sasaki and Coy, Peptides 8: 119 (1987). This method has the advantage of being readily amenable to a large variety of aldehyde components, thus providing a large array of X linker moieties.

A second modular component piece according to the invention comprises an N-protected naturally occurring amine acid or analog thereof, and may be represented by the structural formula

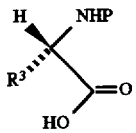

wherein P is a protective group suitable for use in peptide synthesis, and wherein $R^3$=a naturally-occurring amine acid side chain or analog thereof. A completed mimetic may contain none, one, or more second modular component pieces. When more than one second modular component piece is present in a mimetic, additional R groups will be represented in structural formulae as $R^{3'}$.

A third modular component piece according to the invention is characterized by the structural formula

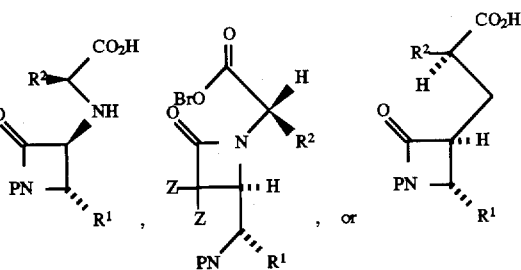

where in P is a protective group suitable for use in peptide synthesis, wherein Z=H or $CH_3$, and wherein $R^1$ and $R^2$=naturally-occurring amino acid side chains or analogs thereof. A preferred protective group is a tert-butyl dimethylsilyl group.

Such a third modular component piece according to the invention may be synthesized by the route shown in Examples 6–8, which entails selective generation of the exocyclic enolate and condensation with an appropriate N-silylimine, followed by mild hydrolysis. See Hart and Hu, Chem. Rev. 89: 1447 or Salzman et al., J. Am. Chem. Soc. 102: 6161 (1980); Miller et al., J. Am. Chem. Soc. 102: 7026 (1990); Williams et al., J. Amer. Chem. Soc. 111: 1073 (1989).

In another aspect, the invention provides a method for producing beta-turn mimetics, comprising generally the steps shown in FIG. 1. Typically, a free amino group coupled to a solid support will be the starting point of the synthesis. The amino group may be coupled to the solid support via a nonpeptide chemical constituent, or it may be the free amino terminus of a nascent peptide being synthesized from the solid support. A first modular component piece according to the invention is coupled via an amide linkage to the free amino group bound to the solid support, to yield a support-bound first modular component piece. A second modular component piece according to the invention is then coupled to the support-bound first modular component piece, using an activated ester coupling to yield a support-bound nascent beta-turn mimetic. A mixed anhydride coupling is then carried out between a third modular component piece and the support-bound nascent beta-turn mimetic to yield a support-band pre-cyclization beta-turn mimetic which is then cyclized to form a support-bound beta-turn mimetic. At this point peptide synthesis may be continued, or the support-bound structure may be cleaved from the support.

Alternatively, synthesis of beta-turn mimetics may be carried out in solution. Synthesis in solution requires essentially the same steps as solid-phase synthesis except that the first modular component piece is not attached to a solid support.

Those skilled in the art will recognize that this method of the invention may be used to synthesize an isolated beta-turn mimetic having variable side chain constituents and backbone size and bond angles, or that it may be readily incorporated into standard Merrifield solid phase peptide synthesis to produce a peptide having such a beta-turn mimetic within it or at either end.

"Beta-turn mimetics" according to the invention actually encompass mimetics of related structures, including gamma turns, beta turns, and beta hairpins. Examples of mimetic gamma turns according to the invention include those represented by the structural formulae

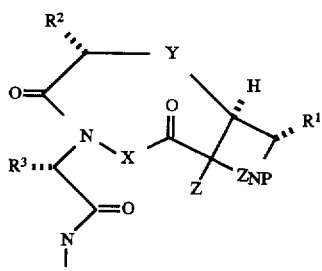

(A)

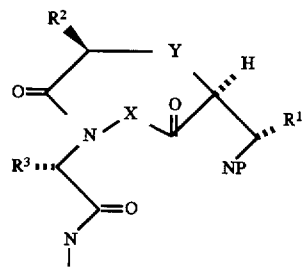

(B)

wherein Z=H or CH₃, and Y=CH₂, NH or NCH₃. Gamma turn mimetics according to the invention are prepared by directly linking together first and third modular component pieces without the use of a second modular component piece.

Mimetics of actual beta-turns, according to the invention, include those represented by the structural formulae

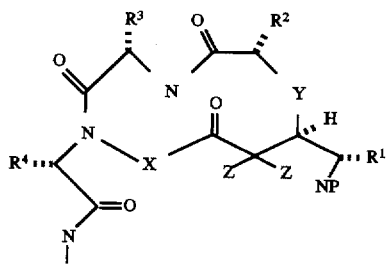

(C)

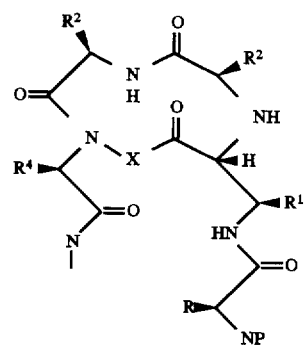

(D)

wherein Y=CH₂, NH or NHCH₃ and Z=H or CH₃.

Examples of beta-hairpin mimetics according to the invention include the following stuctures

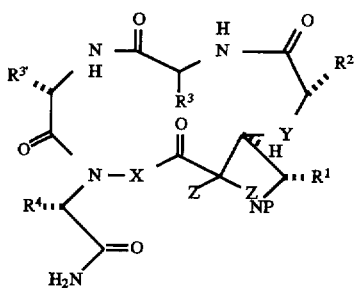

(E)

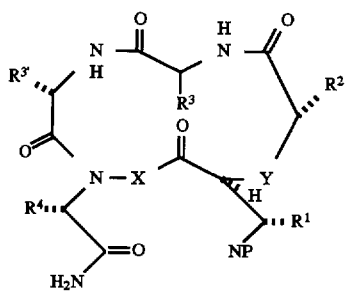

(F)

wherein Y=CH₂, NH or NHCH₃ and Z=H or CH₃. Beta hairpin mimetics according to the invention are prepared by linking two second modular component pieces between the first and third modular component pieces.

In all "beta-turn mimetics", according to the invention, X=a linker group selected from the group described previously.

Thus, in a third aspect, the invention provides both beta-turn mimetics having variable sizes and bond angles and variable side chain constituents, and peptides containing such beta-turn mimetics internally or at either end. Such beta-turn mimetics, or peptides containing the same, are conformationally restricted, and as such are useful for the design and synthesis of conformationally restricted antigens for making synthetic vaccines or for making antibodies for diagnostic purposes. Additionally, they are useful for mapping critical receptor-ligand interactions for purposes of designing nonpeptide therapeutics. They are useful not only for initial mapping, based upon which beta-turn mimetics bind the receptor, but are also useful for subsequent investigation directed toward identification of molecular interactions critical to the binding. For example, if a beta-turn mimetic represented by the structural formula

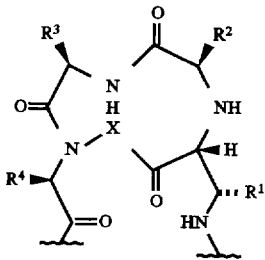

was found to bind to a receptor of interest, the significance of particular hydrogen bonds in its binding can easily be tested by preparing an analog of the beta-turn mimetic that cannot form these bonds, for example

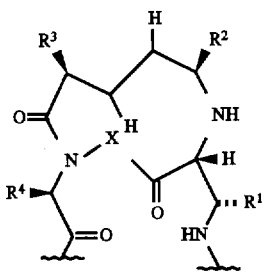

Synthetic nonpeptide molecules can then be produced based upon information obtained from nuclear magnetic resonance (NMR) to determine binding interactions and bound-state conformations of these structures; and employing molecular modeling to interpret the NMR data and to predict improved synthetic nonpeptide structures.

NMR conformational analysis for small peptide and peptide analog systems in solution is straightforward and well known in the art. For example, see Bax, *Two-Dimensional Nuclear Magnetic Resonance in Liquids*, D. Reidel Publishing Co., Boston, 1982; Wuthrich, *NMR of Proteins and Nucleic Acids*, Wiley-Interscience, New York, 1986; Ernst et al., *Principles of Nuclear Magnetic Resonance in One and Two Dimensions*, Oxford University Press, New York, 1987.

NMR along with computer-assisted molecular modeling allows the identification of ligand-receptor interactions required for binding. Identifying the interactions required for binding facilitates preparation of synthetic molecules that are capable of similar binding, and therefore of acting as agonists or antagonists. Once a single stable binding conformation is known, the design and preparation of a synthetic therapeutic molecule capable of acting as an agonist or antagonist is thus brought within the ability of one skilled in the art, without requiring undue experimentation.

Thus, in a fourth aspect, the invention provides synthetic therapeutic molecules capable of acting as agonists or antagonists, wherein such molecules are based upon structural features of a conformationally restricted beta-turn mimetic that is capable of binding to the receptor. Particularly likely candidates for the development of such therapeutics include synthetic molecules based upon one or more structural features of a binding conformation of a peptide hormone, lymphokine, growth factor, enzyme inhibitor, or viral binding protein.

The following examples are intended to further illustrate the invention, and are not limiting in nature.

EXAMPLE 1

Synthesis of a First Modular Component Piece

First modular component pieces were synthesized according to the following scheme.

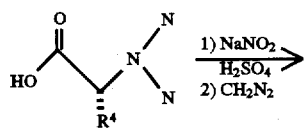

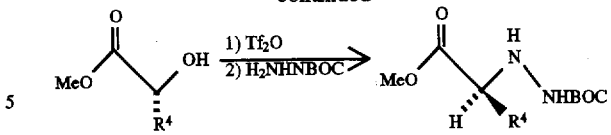

See Hoffman and Kim, Tetrahedron Lett. 31: 2953 (1990).

EXAMPLE 2

Aldehyde Synthesis from Corresponding Carboxylic Acid

Aldehydes were synthesized from their corresponding carboxylic acids according to the following scheme.

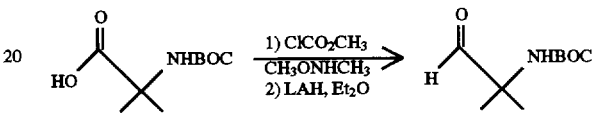

See Goel et al., Org. Syn. 67: 69 (1988).

EXAMPLE 3

Wittig Reaction Homologation of Aldehydes

Homologation of aldehydes was carried out using the Wittig reaction, according to the following scheme.

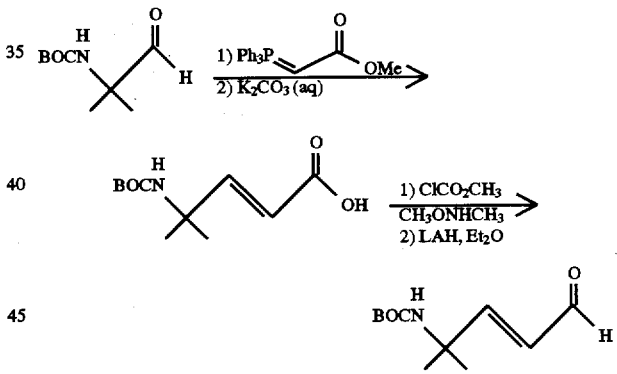

House and Rasmusson, J. Org. Chem. 26: 4278 (1961).

EXAMPLE 4

Alternative Homologation or Aldehydes

Homologation of aldehydes was alternatively carried out according to the following scheme.

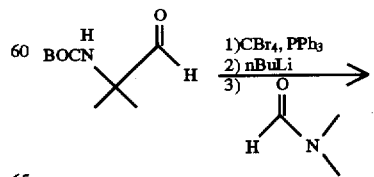

-continued

See, Tetrahedron Lett.: 3769 (1972).

EXAMPLE 5

Cis-Isomerization by Lindler Reduction of Acetylene

Acetylenes prepared according to Example 4 were used in the Lindlar reduction to prepare cis-isomers.

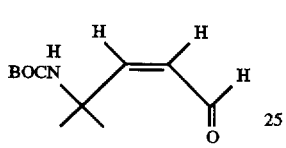

See Lindlar, Helv. Chim. Acta 35: 446 (1952). For reductive animation, see Gribble et al., Organic Prep. Proced. Int. 17: 317 (1985).

EXAMPLE 6

Synthesis of Third Modular Component Pieces

Third modular component pieces were synthesized according to the following scheme.

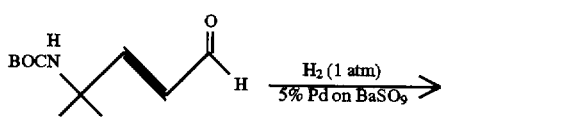

See Hart and Hu, Chem. Rev. 89: 1447 (1990). Third modular component pieces synthesized according to this example are used to create mimetics wherein $R^2$ is attached to a carbon atom adjacent to a tertiary nitrogen.

EXAMPLE 7

Alternative Synthesis of Third Modular Component Pieces

Third modular component pieces were alternatively synthesized according to the following scheme.

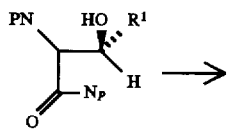

-continued

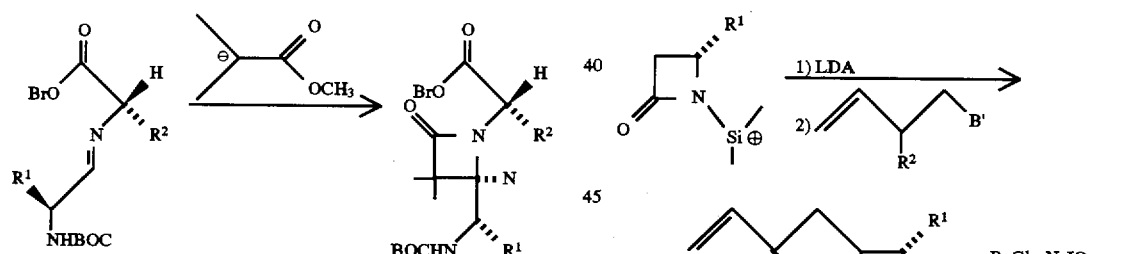

See Miller et al., J. Am. Chem. Soc. 102: 7026 (1980). Third modular component pieces synthesized according to this example are use to create mimetics having $R^2$ attached to a carbon atom adjacent to a secondary nitrogen atom.

EXAMPLE 8

Additional Alternative Synthesis of Third Modular Component Pieces

Third modular component pieces were further synthesized according to the following scheme.

See Williams et al., J. Amer. Chem. Soc. 111: 1073 (1989). Third modular component pieces synthesized according to this example are used to create mimetics having $R^1$ attached to a carbon atom adjacent to a secondary or tertiary nitrogen atom.

EXAMPLE 9

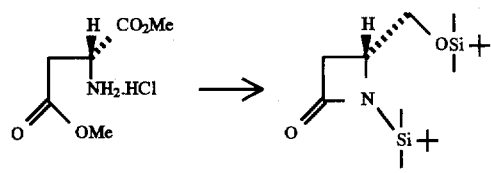

Preparation of N-butyldimethylsilyl-4-(R)-t-butyldimethyl-silyloxy-2-azetidinone 1

D-aspartic acid dimethylester hydrochloride (2.00 g, 10.1 mmol), t-butyldimethylsilyl chloride (1.68 g, 11.1 mmol) and 4-dimethylaminopyridine (62 mg, 0.51 mmol) were dissolved in 50 ml of methylene chloride. To this mixture was added triethylamine (3.24 ml, 23.3 mmol) at room temperature slowly and the mixture was allowed to stir overnight at room temperature. The mixture was washed with aqueous ammonium chloride, saturated sodium bicarbonate and brine, dried over sodium sulfate and concentrated in vacuo. The residue was dissolved in 50 ml of ether. The solution was cooled to 0° C. and 2.0M t-butylmagnesium chloride in ether (5.24 ml, 10.5 mmol) was added dropwise. The mixture was allowed to warm to room temperature overnight with stirring and was coooled to 0° C. again. Saturated ammonium chloride was added and the mixture was stirred for 30 min. Water was added to the mixture and the organic layer was separated. The aqueous layer was extracted with ether (2×30 ml). The combined organic extracts were washed with brine, dried over magnesium sulfate and concentrated in vacuo. The residue was dissolved in 60 ml of methanol. To this solution at room temperature, sodium borohydride (1.14 g, 30.1 mmol) was added to a flask equipped with a reflux condenser. The mixture began to reflux during the addition and ceased after 20 min. After 45 min. in total, the mixture was cooled to 0° C. and aqueous ammonium chloride was added. The mixture was extracted with methylene chloride (3×50 ml). The combined organic extracts were dried over sodium sulfate and the volatiles were removed in vacuo. The residue was dissolved in 30 ml of methylene chloride. To this solution was added t-butyl-dimethylsilyl chloride (1.00 g, 6.63 mmol) and 4-dimethylamino-pyridine (37 mg, 0.30 mmol). Triethylamine (1.10 ml, 7.87 mmol) was added slowly and the mixture was allowed to stir overnight at r.t. The mixture was washed with aq. ammonium chloride and brine, dried over sodium sulfate and concentrated in vacuo. Flash chromatography of the residue on silica-gel with hexane-ethyl acetate (9/1:v/v) afforded 1.01 g (30%) of 1 as a colorless liquid. H NMR (400 MHz, CDCl$_3$ delta 3.74 (dd, J$_a$=3.96 Hz, J$_b$=10.30 Hz, 1H), 3.63 (dd, J$_a$=5.12 Hz, J$_b$=10.30 Hz, 1H), 3.59 (m, 1H), 3.04 (dd, J$_b$=5.28 Hz, J$_b$=15.22 Hz, 1H), 2.76 (dd, J$_a$=2.49 Hz, J$_b$=15.22 Hz, 1H), 0.94 (s, 9H), 0.88 (s, 9H), 0.22 (s, 3H), 0.21 (s, 3H), 0.05 (S, 6H); $^{13}$C NMR (100 MHz, CDCl$_3$): delta 172.7, 65.3, 50.2, 41.2, 26.2, 25.8, −5.4, −5.5, −5.7.

EXAMPLE 10

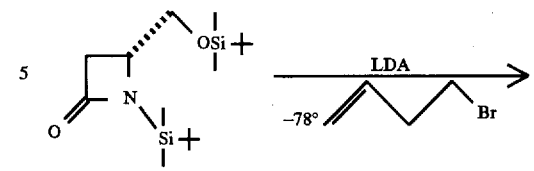

A solution of lithium diisopropyl amide (2.5 mmol in 25 ml of THF) was prepared in the usual manner at 0°. After cooling to −78° C., a solution of azetidinone 5 (323 mg, 1 mmol) in 10 ml of THF was added dropwise and allowed to stir for 30 minutes at −78° C. To this was added 400 ml (4 mmol) of butenyl bromide. Stirring was continued for 18 h. and the reaction allowed to come to room temperature. The reaction mixture was poured into saturated NH$_4$Cl solution and extracted 3 times with 50 ml portions or ether, dried over Na$_2$SO$_4$ and the solvent removed in vacuo. The residue was chromatographed on 15 g or silica gel to provide 294 mg, 78% or azetidinone 6.

EXAMPLE 11

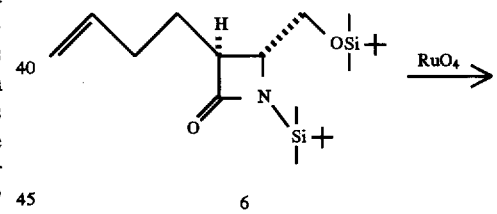

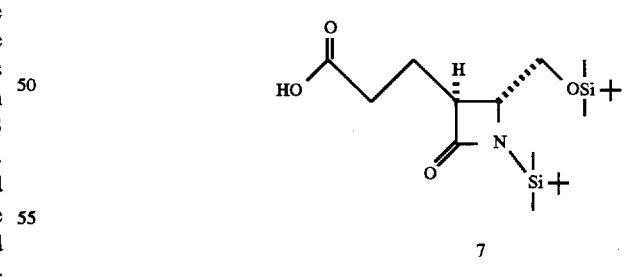

A flask was charged with a magnetic stirrer, CCl$_4$/CH$_3$CN/H$_2$O (1:1:2, total 4 ml), azetidinone 6 (160 mg, 0.44 mmol) and NaIO$_4$ (469 mg, 2.2 mmol, 5 eq). To this biphasic solution, a catalytic amount of RuCl$_3$ 3H$_2$O was added. The mixture was stirred overnight at room temperature and taken up in ethyl acetate (25 ml) and H$_2$O (10 ml). The organic layer was separated and the aqueous layer was saturated with sodium chloride (solid) and extracted with ethyl acetate (2×20 ml). The combined organic extracts were dried over Na$_2$SO$_4$ and concentrated to provide 7 as an oil in 55–65% yield.

I claim:

1. A method for making a gamma-turn mimetic having the structure

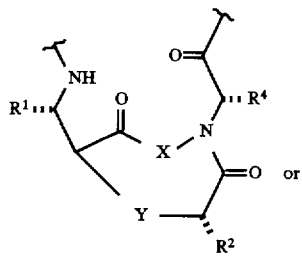

or

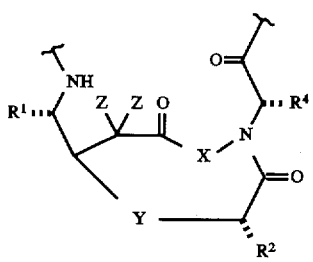

wherein Y is selected from —CH$_2$— and —NH—, and R$^1$, R$^2$, R$^4$, X and Z are as identified below, comprising:

(a) coupling a first modular component piece to a third modular component piece to yield a pre-cyclized gamma-turn mimetic, wherein the first modular component piece has the structure:

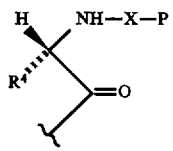

where R$^4$ is a naturally-occurring amino acid side chain substituent or analog thereof, P is a protective group suitable for use in peptide synthesis, and X is a linker moiety terminating in an amino or hydrazino group; and wherein the third modular component piece is selected from the structures:

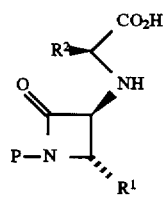

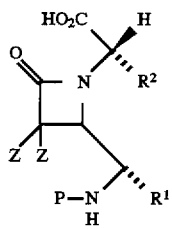

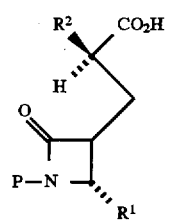

where R$^1$ and R$^2$ are naturally occurring amino acid side chain substituents or analogs thereof, Z is hydrogen or —CH$_3$ and P is a protective group suitable for use in peptide synthesis; and (b) cyclizing the pre-cyclized gamma-turn mimetic to yield the gamma-turn mimetic.

2. The method of claim 1 wherein X is selected from the group of linker moieties listed in FIG. 2.

3. The method of claim 1 wherein X is a linker moiety selected from the group —NH—, —NHC(R$_2$)CH$_2$—, —NHC(R$_2$)CH$_2$CH$_2$CH$_2$— and —NHC(R$_2$)CH=CHCH$_2$—, where each R moiety is individually selected from —H and —CH$_3$.

4. The method of claim 1 wherein the gamma-turn mimetic has the structure:

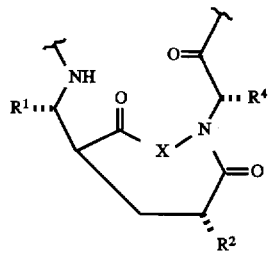

5. The method of claim 1 wherein the gamma-turn mimetic has the structure:

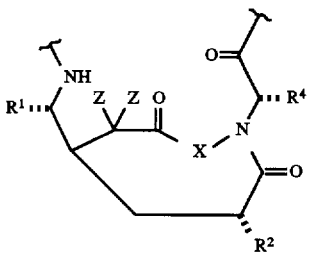

6. The method of claim 1 wherein the gamma-turn mimetic has the structure:
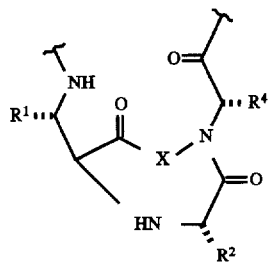
7. The method of claim 1 wherein the gamma-turn mimetic has the structure:
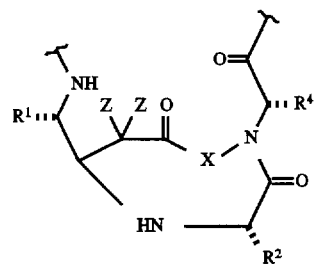
8. A gamma-turn mimetic made according to the method of any one of claim 1.
* * * * *